(12) United States Patent
Cristalli

(10) Patent No.: US 7,517,888 B2
(45) Date of Patent: Apr. 14, 2009

(54) A₁ ADENOSINE RECEPTOR ANTAGONISTS

(75) Inventor: Gloria Cristalli, Camerino (IT)

(73) Assignee: CV Therapeutics, Inc., Palo Alto, CA (US)

( * ) Notice: Subject to any disclaimer, the term of this patent is extended or adjusted under 35 U.S.C. 154(b) by 404 days.

(21) Appl. No.: 11/119,305

(22) Filed: Apr. 28, 2005

(65) Prior Publication Data
US 2005/0245546 A1 Nov. 3, 2005

Related U.S. Application Data

(60) Provisional application No. 60/565,972, filed on Apr. 28, 2004.

(51) Int. Cl.
*C07D 473/34* (2006.01)
*A61K 31/52* (2006.01)
*A61P 13/12* (2006.01)

(52) U.S. Cl. .................... 514/263.4; 544/277
(58) Field of Classification Search ............... 544/277; 514/263.4
See application file for complete search history.

(56) References Cited

U.S. PATENT DOCUMENTS

| | | | |
|---|---|---|---|
| 4,728,644 A | 3/1988 | Yuki et al. | |
| 4,742,064 A * | 5/1988 | Vince ................ | 514/261.1 |
| 5,300,509 A | 4/1994 | Block et al. | |
| 6,841,549 B1 | 1/2005 | Asano et al. | |
| 2005/0090472 A1 | 4/2005 | Yoshida et al. | |
| 2008/0161327 A1* | 7/2008 | Minaskanian et al. .... | 514/263.4 |

FOREIGN PATENT DOCUMENTS

| | | |
|---|---|---|
| EP | 970696 A1 * | 1/2000 |
| WO | WO-03/031406 A2 | 4/2003 |
| WO | WO 2004013141 A | 2/2004 |

OTHER PUBLICATIONS

Taylor et al., Journal of Organic Chemistry (1971), 36(21), 3211-17.*
Klotz et al, "9-Ethyladenine Derivatives as Adenosine Receptor Antagonists: 2- and 8-Substitution Results in Distinct Selectivities" Naunyn-Schmiedeberg's Archives of Pharmacology, Springer, vol. 367, No. 6; Berlin, DE; May 7, 2003; pp. 629-634.

Young et al, "Purine Derivatives as Competitive Inhibitors of Human Erythrocyte Membrane Phosphatidylinositol 4-Kinase"; Journal of Medicinal Chemistry, American Chemical Society; vol. 33, No. 8; Washington, US, Aug. 1, 1990; pp. 2073-2080.
Chin et al, "Reactions of Benzenediazonium Ions with Adenine and its Derivatives"; Journal of Organic Chemistry, vol. 46, No. 11; Chicago, IL, US; May 22, 1981; pp. 2203-2207.
Gannett, et al, "C8-Arylguanidine and C8-Aryladenine Formation if Calf Thymus DNA from Arenediazonium Ions"; Chem. Res. Toxicol., vol. 12, Feb. 13, 1999; pp. 297-304.
El Khadem et al, "Synthesis of 8-(hydroxyalkyl) adenines", Carbohydrate Research, vol. 34, Amsterdam, The Netherlands, Jan. 24, 1974; pp. 203-207.
Giner-Sorolla et al, "Synthesis and Screening of 8-(4'-Thiazolyl)purines", vol. 21, No. 4; 1978, pp. 344-348.
R.F. Bruns et al., "Solubilities of Adenosine Antagonists Determined by Radioreceptor Assay", J. Pharm. Pharmacol. (1989) 41:590-594.
E.A. Falco et al., "Studies on Condensed Pyrimidine Systems. X. Some 1,3-Oxazolo(5,4-d)pyrimidines", J. Am. Chem. Soc. (1952) 74:4897-4902.
H. Harada et al., "2-Alkynyl-8-aryl-9-methyladenines as Novel Adenosine Receptor Antagonists: Their Synthesis and Structure ... ", J. Med. Chem. (2001) 44:170-179.
European Patent Office, "Communication pursuant to Article 96(2) EPC" (Apr. 16, 2007) Application No. 05 742 142.2.

* cited by examiner

*Primary Examiner*—Mark L Berch
(74) *Attorney, Agent, or Firm*—Michael J. Beck; J. Elin Hartrum; CV Therapeutics, Inc.

(57) ABSTRACT

Disclosed are A₁ adenosine receptor antagonists having the general formula

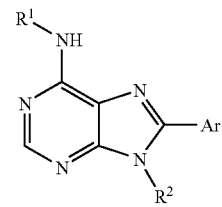

The compounds are useful for treating various disease states, in particular disease states for which diuretic treatment is appropriate.

30 Claims, No Drawings

A₁ ADENOSINE RECEPTOR ANTAGONISTS

CROSS REFERENCE TO RELATED APPLICATIONS

This application claims priority to U.S. Provisional Patent Application Ser. No. 60/565,972, filed Apr. 28, 2004, the complete disclosure of which is hereby incorporated by reference.

FIELD OF THE INVENTION

This invention relates to pharmacology and medicinal chemistry. More particularly, the invention relates to $A_1$ adenosine receptor antagonists, pharmaceutical compositions comprising these compounds and methods of using the same in the treatment of diseases.

BACKGROUND OF THE INVENTION

Adenosine is a nucleoside that occurs naturally in mammals. The heart, for instance, produces and releases adenosine in order to modulate heart rate and coronary vasodilation. Likewise, adenosine is produced in the kidney to modulate essential physiological responses, including glomerular filtration rate (GFR), electrolyte reabsorption, and renin secretion.

Adenosine exerts its biological effects by interacting with a family of adenosine receptors identified as $A_1$, $A_{2a}$, $A_{2b}$, and $A_3$, all of which modulate important physiological processes. For example, $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, *Drug Dev Res* 45:198; Feoktistov et al., *Trends Pharmacol Sci* 19:148-153), and $A_3$ adenosine receptors modulate cell proliferation processes.

Adenosine elicits a response in the kidney through the adenosine $A_1$-receptor. Activation of the adenosine $A_1$ receptor in the kidney stimulates sodium reabsorption from the tubular lumen, and also constricts the afferent arterioles, providing an increase in renal vascular resistance, which leads to a decrease in GFR. Conversely, blockade of the $A_1$ adenosine receptor decreases afferent arteriole pressure, leading to an increase in GFR and urine flow, and sodium excretion.

Decreases in renal function are frequently seen in patients with congestive heart failure (CHF). This phenomenon has been treated with loop diuretics such as furosemide, but it has been shown that use of such diuretics decreases GFR, which is a very undesirable consequence in patients already compromised with CHF.

Accordingly, it is desired to provide highly selective $A_1$ adenosine receptor antagonists, thus avoiding the side effects associated with the biological effects of interaction with the $A_{2a}$, $A_{2b}$, and $A_3$ adenosine receptors. Such compounds would be useful as diuretics that promote sodium excretion, are GFR sparing, and particularly useful in the treatment of CHF.

SUMMARY OF THE INVENTION

It is an object of this invention to provide $A_1$ adenosine receptor antagonists. Accordingly, in a first aspect, the invention relates to compounds of Formula I:

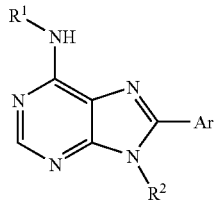

Formula I wherein:
  $R^1$ is hydrogen, optionally substituted $C_4$-$C_{10}$ alkyl, optionally substituted $C_3$-$C_8$ heteroalkyl, or optionally substituted $C_3$-$C_8$ cycloalkyl;
  $R^2$ is hydrogen or $C_1$-$C_6$ alkyl; and
  Ar is optionally substituted aryl or heteroaryl.

A second aspect of this invention relates to pharmaceutical formulations, comprising a therapeutically effective amount of a compound of Formula I and at least one pharmaceutically acceptable excipient.

A third aspect of this invention relates to a method of using the compounds of Formula I in the treatment of a disease or condition in a mammal that can be usefully treated with an $A_1$ adenosine receptor antagonist, comprising administering to a mammal in need thereof a therapeutically effective dose of a compound of Formula I. Such diseases include, but are not limited to, congestive heart failure, chronic renal disease, cirrhosis, or any disease that may be treated with a diuretic.

Preferred compounds of Formula I include those compounds in which $R^1$ is optionally substituted $C_4$-$C_6$ cycloalkyl or $C_4$-$C_6$ heteroalkyl, especially optionally substituted cyclopentyl or cyclohexyl, and $R^2$ is $C_{1-4}$ alkyl, and Ar is an optionally substituted monocyclic aryl or heteroaryl structure. Within this group, preferred compounds include those in which Ar is aryl, especially optionally substituted phenyl.

At present, the preferred compounds include, but are not limited to:
  9-methyl-8-phenylpurine-6-ylamine;
  9-ethyl-8-phenylpurine-6-ylamine;
  8-phenyl-9-propylpurine-6-ylamine;
  (9-methyl-8-phenylpurin-6-yl)oxolan-3-ylamine;
  (9-ethyl-8-phenylpurin-6-yl)oxolan-3-ylamine;
  oxolan-3-yl(8-phenyl-9-propylpurin-6-yl) amine;
  cyclobutyl(9-methyl-8-phenylpurin-6-yl)amine;
  cyclobutyl(9-ethyl-8-phenylpurin-6-yl)amine;
  cyclobutyl(8-phenyl-9-propylpurin-6-yl)amine;
  cyclopentyl(9-methyl-8-phenylpurin-6-yl)amine;
  cyclopentyl(9-ethyl-8-phenylpurin-6-yl)amine;
  cyclopentyl(8-phenyl-9-propylpurin-6-yl)amine;
  cyclohexyl(9-methyl-8-phenylpurin-6-yl) amine;
  cyclohexyl(9-ethyl-8-phenylpurin-6-yl)amine;
  cyclohexyl(8-phenyl-9-propylpurin-6-yl)amine;
  cyclopentyl[9-methyl-8-(2-methylphenyl)purin-6-yl]amine;
  cyclopentyl[9-methyl-8-(3-methylphenyl)purin-6-yl]amine;
  cyclopentyl[9-methyl-8-(4-methylphenyl)purin-6-yl]amine;
  [8-(2-chlorophenyl)-9-methylpurin-6-yl]cyclopentylamine;
  [8-(3-chlorophenyl)-9-methylpurin-6-yl]cyclopentylamine;
  [8-(4-chlorophenyl)-9-methylpurin-6-yl]cyclopentylamine;

cyclopentyl[8-(4-fluorophenyl)-9-methylpurin-6-yl]
amine;

cyclopentyl[8-(4-methoxyphenyl)-9-methylpurin-6-yl]
amine;

4-[6-(cyclopentylamino)-9-methylpurin-8-yl]phenol; and cyclopentyl(9-methyl-8-(3-pyridyl)purin-6-yl)amine.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or 2) an alkyl group as defined above that is interrupted by 1-10 atoms independently chosen from oxygen, sulfur and NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both 1, 2, 3, 4, and 5 substituents as defined above and is also interrupted by 1-10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1-10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1, 2, 3, 4, 5, or 6 carbon atoms.

The term "lower alkylene" refers to a diradical of a branched or unbranched saturated hydrocarbon chain, preferably having from 1, 2, 3, 4, 5, or 6 carbon atoms.

The term "substituted alkylene" refers to:

(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or (2) an alkylene group as defined above that is interrupted by 1-20 atoms independently chosen from oxygen, sulfur and NR$_a$—, where R$_a$ is chosen from hydrogen, optionally substituted alkyl, cycloalkyl, cycloalkenyl, aryl, heteroaryl and heterocyclyl, or groups selected from carbonyl, carboxyester, carboxyamide and sulfonyl; or (3) an alkylene group as defined above that has both 1, 2, 3, 4, or 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH=CH$_2$), 1-propylene or allyl (—CH$_2$CH=CH$_2$), isopropylene, (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, CF$_3$, amino, substituted amino, cyano, or —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained by the definition for the aryl or arylene substituent, such aryl or arylene groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl, Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to carbocyclic groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroarylene" refers to a diradical of a heteroaryl group as defined above. This term is exemplified by groups such as 2,5-imidazolene, 3,5-[1,2,4]oxadiazolene, 2,4-oxazolene, 1,4-pyrazolene, and the like. For example, 1,4-pyrazolene is:

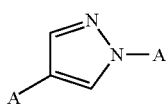

where A represents the points of attachment.

Unless otherwise constrained by the definition for the heteroaryl or heteroarylene substituent, such heteroaryl or heterarylene groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, prodrugs, hydrates and polymorphs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
 (i) preventing the disease, that is, causing the clinical symptoms of the disease not to develop;
 (ii) inhibiting the disease, that is, arresting the development of clinical symptoms; and/or
 (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

NOMENCLATURE

The naming and numbering of the compounds of the invention is illustrated with a representative compound of Formula I in which $R^1$ is cyclohexyl, $R^2$ is hydrogen, $R^3$ is methyl, and $R^4$ is phenyl:

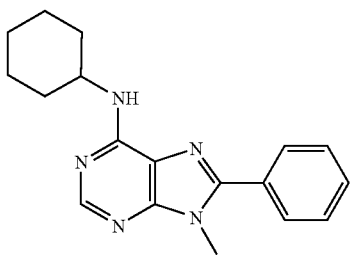

namely, cyclohexyl(9-methyl-8-phenylpurin-6-yl)amine.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The compounds of the invention may be synthesized using conventional synthetic methods. Suitable reactions and methods will be obvious to those of skill in the art. Examples of such methods may be found in references such as *Tetrahedron*, 48(48), 10637-44; 1992, *Journal of Organic Chemistry*, 55(8), 2451-7; 1990, *Helvetica Chimica Acta*, 72(2), 271-7; 1989, *Polish Journal of Chemistry*, 61(7-21), 901-6; 1987, and *Journal of the Chemical Society, Perkin Tansactions 1: Organic and Bio-Organic Chemistry* (1972-1999), (5), 879-85; 1984.

The term "q.s." means adding a quantity sufficient to achieve a stated function, e.g., to bring a solution to the desired volume (i.e., 100%).

Synthesis of the Compounds of Formula I

The compounds of Formula I are prepared as shown in Reaction Scheme I.

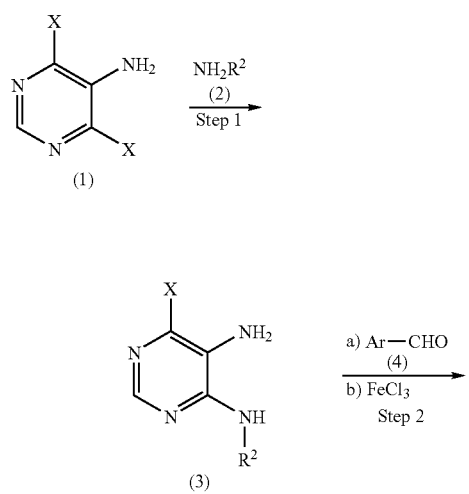

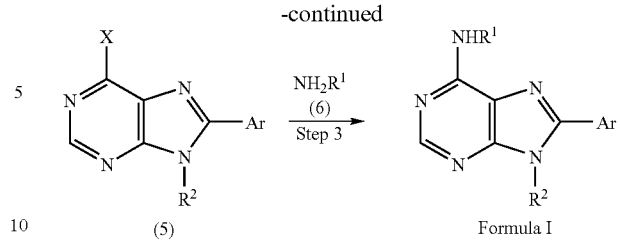

Step 1: Preparation of Formula (3):

A compound of formula (3) is prepared by reacting a suitable amine (2) with a 4,6-dihalo-pyrimidin-5-yl-amine, shown as formula (1) in Reaction Scheme I. Typically, the reaction is carried out by first dissolving the amine in a polar solvent such as ethanol along with a catalytic amount of triethylamine. The formula (2) amine is then added to this solution. The reaction mixture is heated to approximately 60-100° C. for about 2 to 5 hours. The solvent is then removed using conventional methods such as rotary evaporation.

The amine (2) compounds are commercially available as are the 4,6-dihalo-pyrimidine-5-yl-amines (1). Suitable amines include, but are not limited to, methylamine, ethylamine, propylamine, t-butylamine, etc. Suitable formula (2) amines include, but are not limited to 4,6-dichloro-pyrimidien-5-yl-amine.

Step 2: Preparation of Formula (5):

The formula (5) compounds are prepared in a two-step process. As an initial step, the compound of formula (3) is reacted with an optionally substituted aryl-aldehyde such as benzylaldehyde, 4-methylbenzyladehyde, 3-chlorobenxyladehyde, or the like. These compounds are indicated as formula (4) in Reaction Scheme I. The reaction takes place in acidic polar solution, i.e., a methanol/acetic acid solution, and is conducted at room temperature for 1 to 2 days.

Once this initial step has taken place, the reaction mixture is concentrated to dryness and the resulting crude imine is collected via azeotropic distillation in a suitable solvent such as toluene. This imine is then placed in a solution of $FeCl_3$ in ethanol and stirred at approximately 80° C. for 2-6 hours. The solvent may then be removed and the formula (5) compound further purified via silica gel chromatography and/or crystallization.

Step 3: Preparation of Formula (I):

It will be appreciated by those of skill in the art that any number of methods may be used to synthesize the Formula (I) compounds from the formula (5) intermediate produced in the previous step.

In instances where $R^1$ is hydrogen, the Formula (I) compound may be produced by reacting the formula (5) intermediate with ammonia. Generally, the ammonia will be cooled prior to mixing with the formula (5) intermediate. The mixture is then stirred at 2-20° C. for 20-40 hours. Once the reaction is complete, the ammonia is allowed to evaporate at room temperature and the residue chromatographed and/or crystallized to give the Formula (I) compound.

When the $R^1$ moiety is other than hydrogen, the Formula (I) compounds may be synthesized by solubilizing the formula (5) intermediate in THF followed by addition of an amine of formula (6) having the desired $R^1$ moiety. A tertiary amine such as triethylamine is also added to the solution. Once the final solution is prepared, it is stirred at 60-90° C. for 20-40 hours. After in vacuo evaporation of volatiles, the reaction mixture may be chromatographed on silica gel column eluting with the suitable solvent to give, after crystallization, a compound of Formula (I).

Of course, dependent upon the desired $R^1$ moiety, formation of the Formula (I) compounds carried out without the need for the proton accepting tertiary amine. For example, compounds such as cyclopentylamine may be placed in solution with the solubilized formula (5) intermediate and the reaction mixture then stirred at room temperature for 5-10 hours. The solvent may then be evaporated and the Formula (I) compound purified as described above.

UTILITY, TESTING AND ADMINISTRATION

General Utility

The compounds of Formula I are effective in the treatment of conditions that respond to administration of $A_1$ adenosine receptor antagonists. Such conditions include, but are not limited to, disease states for which diuretic treatment is appropriate, renal failure, nephritis, hypertension, edemas, Alzheimers disease, stress, depression, cardiac arrhythmia, restoration of cardiac function, asthma, respiratory disorders, ischemia-induced injury of the brain, heart and kidney, diarrhea, and disease states for which antilipolytic treatment is appropriate.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Compounds of Formula I may be impregnated into a stent by diffusion, for example, or coated onto the stent such as in a gel form, for example, using procedures known to one of skill in the art in light of the present disclosure.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper, or other container. When the excipient serves as a diluent, it can be in the form of a solid, semi-solid, or liquid material (as above), which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methylcellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and are generally administered in a pharmaceutically effective amount. Preferably, for oral administration, each dosage unit contains from 1 mg to 2 g of a compound of Formula I, and for parenteral administration, preferably from 0.1 to 700 mg of a compound of Formula I. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills, and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous, or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

A. Preparation of a Compound of Formula (3) in which $R^2$ is Methyl

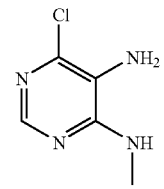

To 1 mL of methylamine, cooled at −80° C. in a steel vial, ethanol (13 mL) and triethylamine (1.3 mL) were added. Commercially available 4,6-dichloro-pyrimidin-5-yl-amine (3.0 mmol) was added to the solution and the reaction mixture heated at 80° C. for 3 hours. The solvent was removed in vacuo, and the resulting compound, (5-amino-6-chloropyrimidin-4-yl)methylamine, was obtained after silica gel chromatography and/or crystallization.

B. Preparation of other Compounds of Formula (3)

Similarly, by replacing methylamine with other amines, the following compounds of formula (3) were or can be made:
(5-amino-6-chloropyrimidin-4-yl)ethylamine;
(5-amino-6-chloropyrimidin-4-yl)propylamine; and
(5-amino-6-chloropyrimidin-4-yl)(methylethyl)amine.

EXAMPLE 2

A. Preparation of a Compound of Formula (5) were $R^2$ is Methyl and Ar is Phenyl

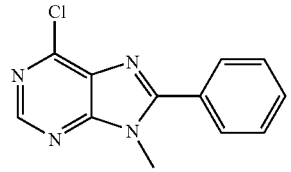

A solution of (5-amino-6-chloropyrimidin-4-yl)methylamine (1 mmol), benzaldehyde (1.2 mmol), and acetic acid (2.3 mmol) in methanol (4.3 mL) was stirred at room temperature for 32 hours. The reaction mixture was concentrated to dryness under reduced pressure and the residue azeotropically distilled with toluene (4 mL×2).

The residue was suspended in ethanol (6 mL) and a solution of $FeCl_3$ (160 mg) in ethanol (3 mL) was then added. The mixture was stirred at 80° C. for 4 hours. The solvent was removed and 6-chloro-9-methyl-8-phenylpurine obtained as a pure compound after silica gel chromatography and crystallization.

B. Preparation of Other Compounds of Formula (5) where R² is not Methyl

Similarly, by replacing (5-amino-6-chloropyrimidin-4-yl) methylamine with other amines of formula (3), the following compounds of formula (5) were or can be made:

6-chloro-9-ethyl-8-phenylpurine;
6-chloro-8-phenyl-9-propylpurine; and
6-chloro-9-(methylethyl)-8-phenylpurine.

C. Preparation of Other Compounds of Formula (5) where Ar is not Unsubstituted Phenyl Similarly, by replacing benzaldehyde with other optionally substituted aryl-aldehydes of formula (4), the following compounds of formula (5) were made:

6-chloro-9-methyl-8-(2-methylphenyl)purine;
6-chloro-9-methyl-8-(3-methylphenyl)purine;
6-chloro-9-methyl-8-(4-methylphenyl)purine;
6-chloro-8-(2-chlorophenyl)-9-methylpurine;
6-chloro-8-(3-chlorophenyl)-9-methylpurine;
6-chloro-8-(4-chlorophenyl)-9-methylpurine;
6-chloro-8-(4-fluorophenyl)-9-methylpurine;
1-(6-chloro-9-methylpurin-8-yl)-4-methoxybenzene;
4-(6-chloro-9-methylpurin-8-yl)phenol;
4-(6-chloro-9-methylpurin-8-yl)benzoic acid; and
6-chloro-9-methyl-8-(3-pyridyl)purine,

EXAMPLE 3

A. Preparation of a Compound of Formula (I) were R¹ is Hydrogen, R² is Methyl, and Ar is Phenyl

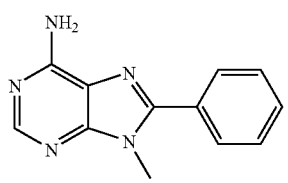

6-chloro-9-methyl-8-phenylpurine was added in a steel vial to ammonia cooled to −196° C. using liquid nitrogen. The reaction mixture was allowed to warm to 16° C. for 70 hours; after that, the ammonia was allowed to evaporate at room temperature and the residue was chromatographed and/or crystallized to give 9-methyl-8-phenylpurine-6-ylamine, a compound of Formula (I).

B. Preparation of Other Compounds of Formula (I) where R² is not Methyl

Similarly, by replacing 6-chloro-9-methyl-8-phenylpurine with other purines of formula (5), the following compounds of Formula (I) were and can be made:

9-ethyl-8-phenylpurine-6-ylamine;
8-phenyl-9-propylpurine-6-ylamine; and
9-(methylethyl)-8-phenylpurine-6-ylamine.

EXAMPLE 4

A. Preparation of a Compound of Formula (I) were R¹ is Oxolan-3-yl, R² is Methyl, and Ar is Phenyl

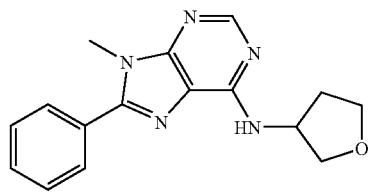

6-chloro-9-methyl-8-phenylpurine (1.0 mmol) was solubilized in 12 mL of dry THF and to the solution was added tetrahydrofuran-3-ylamine toluene-4-sulfonic acid salt (4.0 mmol) and triethylamine (12 mmol). The solution was stirred at 80° C. for 20-40 hours. After in vacuo evaporation of volatiles, the reaction mixture was chromatographed on silica gel column eluting with the suitable solvent to give, after crystallization, (9-methyl-8-phenylpurin-6-yl)oxolan-3-ylamine, a compound of Formula (I).

B. Preparation of Other Compounds of Formula (I)

Similarly, by replacing 6-chloro-9-methyl-8-phenylpurine with other purines of formula (5) and/or replacing tetrahydrofuran-3-ylamine toluene-4-sulfonic acid salt with the salts of other amines of formula (6), the following compounds of Formula (I) were and can be made:

(9-ethyl-8-phenylpurin-6-yl)oxolan-3-ylamine;
oxolan-3-yl(8-phenyl-9-propylpurin-6-yl)amine;
[9-(methylethyl)-8-phenylpurin-6-yl]oxolan-3-ylamine;
cyclobutyl(9-methyl-8-phenylpurin-6-yl)amine;
cyclobutyl(9-ethyl-8-phenylpurin-6-yl)amine;
cyclobutyl(8-phenyl-9-propylpurin-6-yl)amine; and
cyclobutyl[9-(methylethyl)-8-phenylpurin-6-yl]amine.

EXAMPLE 5

A. Preparation of a Compound of Formula (I) were R¹ is Cyclopentyl, R² is Methyl, and Ar is Phenyl

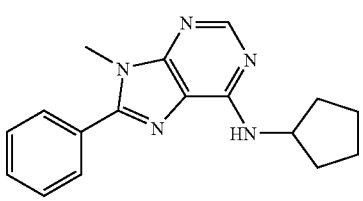

6-chloro-9-methyl-8-phenylpurine (1.0 mmol) was added to cyclopentylamine (10 mL). The reaction mixtures were stirred at room temperature for 5 hours. After that, the solvent was evaporated and pure cyclopentyl(9-methyl-8-phenylpurin-6-yl)amine, a compound of Formula (I), was obtained after silica gel chromatography.

B. Preparation of Other Compounds of Formula (I)

Similarly, by replacing 6-chloro-9-methyl-8-phenylpurine with other purines of formula (5) and/or replacing cyclopentylamine with other amines of formula (6), the following compounds of Formula (I) were made:

cyclopentyl(9-ethyl-8-phenylpurin-6-yl)amine;
cyclopentyl(8-phenyl-9-propylpurin-6-yl)amine;
cyclopentyl(8-phenyl-9-(methylethyl)-purin-6-yl)amine;
cyclohexyl(9-methyl-8-phenylpurin-6-yl)amine;
cyclohexyl(9-ethyl-8-phenylpurin-6-yl)amine;
cyclohexyl(8-phenyl-9-propylpurin-6-yl)amine;
cyclohexyl(8-phenyl-9-(methylethyl)-6-yl)amine;
cyclopentyl[9-methyl-8-(2-methylphenyl)purin-6-yl]amine;
cyclopentyl[9-methyl-8-(3-methylphenyl)purin-6-yl]amine;
cyclopentyl[9-methyl-8-(4-methylphenyl)purin-6-yl]amine;
[8-(2-chlorophenyl)-9-methylpurin-6-yl]cyclopentylamine;
[8-(3-chlorophenyl)-9-methylpurin-6-yl]cyclopentylamine;
[8-(4-chlorophenyl)-9-methylpurin-6-yl]cyclopentylamine;
cyclopentyl[8-(4-fluorophenyl)-9-methylpurin-6-yl]amine;
cyclopentyl[8-(4-methoxyphenyl)-9-methylpurin-6-yl]amine;
4-[6-(cyclopentylamino)-9-methylpurin-8-yl]phenol; and
cyclopentyl(9-methyl-8-(3-pyridyl)purin-6-yl)amine.

EXAMPLE 6

All compounds of Formula I prepared as shown in the above procedures were characterized by NMR. For example:

9-Methyl-8-phenylpurine-6-ylamine: $^1$H-NMR (DMSO-$d_6$) δ 3.81 (s, 3H, CH$_3$); 7.31 (br s, 2H, NH$_2$); 7.58 (m, 3H, H-Ph); 7.88 (m, 2H, H-Ph); 8.19 (s, 1H, H-2).

9-Ethyl-8-phenylpurine-6-ylamine: $^1$H-NMR (DMSO-$d_6$) δ 1.29 (t, 3H, J=7.2 Hz, CH$_3$); 4.25 (q, 2H, J=7.2 Hz, CH$_2$); 7.29 (br s, 2H, NH$_2$); 7.58 (m, 3H, H-Ph); 7.77 (m, 2H, H-Ph); 8.18 (s, 1H, H-2).

8-Phenyl-9-propylpurine-6-ylamine: $^1$H-NMR (DMSO-$d_6$) δ 0.71 (t, 3H, J=7.4 Hz, CH$_3$); 1.65 (m, 2H, CH$_2$CH$_2$CH$_3$); 4.21 (t, 2H, J=7.4 Hz, N—CH$_2$); 7.29 (br s, 2H, NH$_2$); 7.58 (m, 3H, H-Ph); 7.78 (m, 2H, H-Ph); 8.18 (s, 1H, H-2).

(9-Methyl-8-phenylpurin-6-yl)oxolan-3-ylamine: $^1$H-NMR (DMSO-$d_6$) δ 1.28 (t, 3H, J=7.1 Hz, CH$_3$); 2.12 (m, 2H, THF); 3.96-3.79 (m, 4H, THF); 4.25 (q, 2H, J=7.0 Hz, N—CH$_2$); 4.77 (m, 1H, CH-THF); 7.57 (m, 3H, H-Ph); 7.78 (m, 2H, H-Ph); 7.98 (m, 1H, NH); 8.27 (s, 1H, H-2).

(9-Ethyl-8-phenylpurin-6-yl)oxolan-3-ylamine: $^1$H-NMR (DMSO-$d_6$) δ 1.28 (t, 3H, J=7.1 Hz, CH$_3$); 2.12 (m, 2H, THF); 3.96-3.79 (m, 4H, THF); 4.25 (q, 2H, J=7.0 Hz, N—CH$_2$); 4.77 (m, 1H, CH-THF); 7.57 (m, 3H, H-Ph); 7.78 (m, 2H, H-Ph); 7.98 (m, 1H, NH); 8.27 (s, 1H, H-2).

Oxolan-3-yl(8-phenyl-9-propylpurin-6-yl)amine: $^1$H-NMR (DMSO-$d_6$) δ 0.71 (t, 3H, J=7.3, CH$_3$); 1.65 (m, 2H, CH$_2$CH$_2$CH$_3$); 2.00-2.30 (m, 2H, THF); 3.60-3.99 (m, 4H, THF); 4.22 (t, 2H, J=7.4 Hz, N—CH$_2$); 4.75 (m, 1H, CH-THF); 7.58 (m, 3H, H-Ph); 7.78 (m, 2H, H-Ph); 8.00 (m, 1H, NH); 8.27 (s, 1H, H-2).

Cyclobutyl(9-methyl-8-phenylpurin-6-yl)amine: $^1$H-NMR (DMSO-$d_6$) δ 1.68 (m, 2H, H-cyclobutyl); 2.20 (m, 4H, H-cyclobutyl); 3.81 (s, 3H, CH$_3$); 4.75 (m, 1H, CH-cyclobutyl); 7.59 (m, 3H, H-Ph); 7.88 (m, 2H, H-Ph); 8.10 (m, 1H, NH); 8.24 (s, 1H, H-2).

Cyclobutyl(9-ethyl-8-phenylpurin-6-yl)amine: $^1$H-NMR (DMSO-$d_6$) δ 1.28 (t, 3H, J=7.1 Hz, CH$_3$); 1.65 (m, 2H, H-cyclobutyl); 2.21 (m, 4H, H-cyclobutyl); 4.25 (q, 2H, J=7.1 Hz, CH$_2$); 4.72 (m, 1H, CH-cyclobutyl); 7.56 (m, 3H, H-Ph); 7.78 (m, 2H, H-Ph); 8.09 (m, 1H, NH); 8.23 (s, 1H, H-2).

Cyclobutyl(8-phenyl-9-propylpurin-6-yl)amine: $^1$H-NMR (DMSO-$d_6$) δ 0.71 (t, 3H, J=7.5 Hz, CH$_3$); 1.66 (m, 4H, H-cyclobutyl and CH$_2$CH$_2$CH$_3$); 2.09-2.25 (m, 4H, H-cyclobutyl); 4.22 (q, 2H, J=7.0 Hz, N—CH$_2$); 4.75 (m, 1H, CH-cyclobutyl); 7.58 (m, 3H, H-Ph); 7.79 (m, 2H, H-Ph); 8.10 (m, 1H, NH); 8.24 (s, 1H, H-2).

Cyclopentyl(9-methyl-8-phenylpurin-6-yl)amine: $^1$H-NMR (DMSO-$d_6$) δ 1.63 (m, 6H, H-cyclopentyl); 1.96 (m, 2H, H-cyclopentyl); 3.80 (s, 3H, N—CH$_3$); 4.57 (m, 1H, CH-cyclopentyl); 7.57 (m, 3H, H-Ph); 7.73 (d, J=7.8 Hz, NH); 7.87 (m, 2H, H-Ph); 8.24 (s, 1H, H-2).

Cyclopentyl(9-ethyl-8-phenylpurin-6-yl)amine: $^1$H-NMR (DMSO-$d_6$) δ 1.28 (t, 3H, J=7.3 Hz, CH$_3$); 1.62 (m, 6H, H-cyclopentyl); 1.95 (m, 2H, H-cyclopentyl); 4.25 (q, 2H, J=7.3 Hz, N—CH$_2$); 4.57 (m, 1H, CH-cyclopentyl); 7.59 (m, 3H, H-Ph); 7.75 (m, 3H, H-Ph and NH); 8.24 (s, 1H, H-2).

Cyclopentyl(8-phenyl-9-propylpurin-6-yl)amine: $^1$H-NMR (DMSO-$d_6$) δ 0.71 (t, 3H, J=7.3 Hz, CH$_3$); 1.63 (m, 8H, H-cyclopentyl and CH$_2$CH$_2$CH$_3$); 1.96 (m, 2H, H-cyclopentyl); 4.22 (t, 2H, J=7.3 Hz, N—CH$_2$); 4.55 (m, 1H, CH-cyclopentyl); 7.57 (m, 3H, H-Ph); 7.77 (m, 3H, H-Ph and NH); 8.24 (s, 1H, H-2).

Cyclohexyl(9-methyl-8-phenylpurin-6-yl)amine: $^1$H-NMR (DMSO-$d_6$) δ 1.07-1.98 (m, 10H, H-cyclohexyl); 3.80 (s, 3H, CH$_3$); 4.14 (m, 1H, CH-cyclohexyl); 7.58 (m, 4H, H-Ph and NH); 7.87 (m, 2H, H-Ph); 8.23 (s, 1H, H-2).

Cyclohexyl(9-ethyl-8-phenylpurin-6-yl)amine: $^1$H-NMR (DMSO-$d_6$) δ 1.10-1.95 (m, 13H, CH$_3$ and H-cyclohexyl); 4.12 (m, 1H, CH-cyclohexyl); 4.25 (q, 2H, J=7.4 Hz, N—CH$_2$); 7.57 (m, 4H, H-Ph and NH); 7.77 (m, 2H, H-Ph); 8.22 (s, 1H, H-2).

Cyclohexyl(8-phenyl-9-propylpurin-6-yl)amine: $^1$H-NMR (DMSO-$d_6$) δ 0.70 (t, 3H, J=7.3 Hz, CH$_3$); 1.03-1.98 (m, 12H, H-cyclohexyl and CH$_2$CH$_2$CH$_3$); 4.12 (m, 3H, N—CH$_2$ and CH-cyclohexyl); 7.56 (m, 4H, H-Ph and NH); 7.76 (m, 2H, H-Ph); 8.22 (s, 1H, H-2).

Cyclopentyl[9-methyl-8-(2-methylphenyl)purin-6-yl]amine: $^1$H-NMR (DMSO-$d_6$) δ 1.51-1.79 (m, 6H, H-cyclopentyl); 1.95 (m, 2H, H-cyclopentyl); 2.22 (s, 3H, Ph-CH$_3$); 3.49 (s, 3H, N—CH$_3$); 4.55 (m, 1H, CH-cyclopentyl); 7.41 (m, 4H, H-Ph); 7.67 (d, 1H, J=6.6 Hz, NH); 8.24 (s, 1H, H-2).

Cyclopentyl[9-methyl-8-(3-methylphenyl)purin-6-yl]amine: $^1$H-NMR (DMSO-$d_6$) δ 1.48-1.75 (m, 6H, H-cyclopentyl); 1.95 (m, 2H, H-cyclopentyl); 2.41 (s, 3H, Ph-CH$_3$); 3.79 (s, 3H, N—CH$_3$); 4.57 (m, 1H, CH-cyclopentyl); 7.42 (m, 2H, H-Ph); 7.65 (m, 3H, H-Ph and NH); 8.23 (s, 1H, H-2).

Cyclopentyl[9-methyl-8-(4-methylphenyl)purin-6-yl]amine: $^1$H-NMR (DMSO-$d_6$) δ 1.44-1.75 (m, 6H, H-cyclopentyl); 1.95 (m, 2H, H-cyclopentyl); 2.40 (s, 3H, Ph-CH$_3$); 3.78 (s, 3H, N—CH$_3$); 4.55 (m, 1H, CH-cyclopentyl); 7.37 (d, 2H, J=8.0 Hz, H-Ph); 7.67 (d, 1H, J=7.8 Hz, NH); 7.75 (d, 2H, J=8.4 Hz, H-Ph); 8.22 (s, 1H, H-2).

[8-(2-Chlorophenyl)-9-methylpurin-6-yl]cyclopentylamine: $^1$H-NMR (DMSO-$d_6$) δ 1.50-1.75 (m, 6H, H-cyclopentyl); 1.95 (m, 2H, H-cyclopentyl); 3.52 (s, 3H, CH$_3$); 4.55 (m, 1H, CH-cyclopentyl); 7.61 (m, 4H, H-Ph); 7.80 (m, 1H, NH); 8.26 (s, 1H, H-2).

[8-(3-Chlorophenyl)-9-methylpurin-6-yl]cyclopentylamine: $^1$H-NMR (DMSO-$d_6$) δ 1.52-1.75 (m, 6H, H-cyclopentyl); 1.95 (m, 2H, H-cyclopentyl); 3.82 (s, 3H, CH$_3$); 4.55

(m, 1H, CH-cyclopentyl); 7.61 (m, 2H, H-Ph); 7.82 (m, 2H, H-Ph and NH); 7.95 (s, 1H, H-Ph); 8.25 (s, 1H, H-2).

[8-(4-Chlorophenyl)-9-methylpurin-6-yl]cyclopentylamine: $^1$H-NMR (DMSO-$d_6$) δ 1.47-1.75 (m, 6H, H-cyclopentyl); 1.95 (m, 2H, H-cyclopentyl); 3.80 (s, 3H, $CH_3$); 4.52 (m, 1H, CH-cyclopentyl); 7.64 (m, 2H, H-Ph); 7.78 (d, 1H, J=7.4 Hz, NH); 7.91 (m, 2H, H-Ph); 8.24 (s, 1H, H-2).

Cyclopentyl[8-(4-fluorophenyl)-9-methylpurin-6-yl]amine: $^1$H-NMR (DMSO-$d_6$) δ 1.50-1.72 (m, 6H, H-cyclopentyl); 1.97 (m, 2H, H-cyclopentyl); 3.79 (s, 3H, $CH_3$); 4.58 (m, 1H, CH-cyclopentyl); 7.42 (m, 2H, H-Ph); 7.72 (d, 1H, J=7.6 Hz, NH); 7.93 (m, 2H, H-Ph); 8.24 (s, 1H, H-2).

Cyclopentyl[8-(4-methoxyphenyl)-9-methylpurin-6-yl]amine: $^1$H-NMR (DMSO-$d_6$) δ 1.50-1.75 (m, 6H, H-cyclopentyl); 1.95 (m, 2H, H-cyclopentyl); 3.78 (s, 3H, $CH_3$); 3.84 (s, 3H, Ph-$OCH_3$); 4.55 (m, 1H, CH-cyclopentyl); 7.08 (m, 2H, H-Ph); 7.65 (d, 1H, J=7.6 Hz, NH); 7.81 (m, 2H, H-Ph); 8.21 (s, 1H, H-2).

4-[6-(Cyclopentylamino)-9-methylpurin-8-yl]phenol: $^1$H-NMR (DMSO-$d_6$) δ 1.45-1.75 (m, 6H, H-cyclopentyl); 1.94 (m, 2H, H-cyclopentyl); 3.76 (s, 3H, $CH_3$); 4.55 (m, 1H, CH-cyclopentyl); 6.92 (d, 2H, J=8.6 Hz, H-Ph); 7.60 (d, 1H, J=7.6 Hz, NH); 7.69 (d, 2H, J=8.6 Hz, H-Ph); 8.20 (s, 1H, H-2); 9.98 (s, 1H, Ph-OH).

Cyclopentyl(9-methyl-8-(3-pyridyl)purin-6-yl)amine: $^1$H-NMR (DMSO-$d_6$) δ 1.47-1.75 (m, 6H, H-cyclopentyl); 1.96 (m, 2H, H-cyclopentyl); 3.82 (s, 3H, $CH_3$); 4.58 (m, 1H, CH-cyclopentyl); 7.61 (m, 1H, Hc-Py); 7.81 (d, J=7.2 Hz, 1H, NH); 8.29 (m, 2H, Hd-Py and H-2); 8.74 (m, 1H, Hc-Py); 9.06 (m, 1H, Ha-Py).

The following examples illustrate the preparation of representative pharmaceutical formulations containing a compound of Formula I, such as those prepared in accordance with Examples 1-5 above.

EXAMPLE 7

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 8

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 9

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 10

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 11

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 12

Suspensions, each containing 50 mg of active ingredient per 5.0 mL dose are made as follows:

| Ingredient | Amount |
| --- | --- |
| Active Ingredient | 50.0 mg |
| Xanthan gum | |
| Sodium carboxymethyl cellulose (11%) | 4.0 mg |
| Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose, and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 13

A subcutaneous formulation may be prepared as follows:

| Ingredient | Quantity |
| --- | --- |
| Active Ingredient | 5.0 mg |
| Corn Oil | 1.0 mL |

EXAMPLE 14

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

EXAMPLE 15

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 16

Sustained Release Composition

| Ingredient | Weight Range (%) | Preferred Range (%) | Most Preferred Range (%) |
| --- | --- | --- | --- |
| Active ingredient | 50-95 | 70-90 | 75 |
| Microcrystalline cellulose (filler) | 1-35 | 5-15 | 10.6 |
| Methacrylic acid copolymer | 1-35 | 5-12.5 | 10.0 |
| Sodium hydroxide | 0.1-1.0 | 0.2-0.6 | 0.4 |
| Hydroxypropyl methylcellulose | 0.5-5.0 | 1-3 | 2.0 |
| Magnesium stearate | 0.5-5.0 | 1-3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base, which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably, the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 21

Stable Transfection of HEK-293 or CHO Cells

The cDNAs for human $A_1$, $A_{2A}$, $A_{2B}$ or $A_3$ AdoRs were prepared by RT-PCR from total RNA of human cells or tissues and sequenced on both strands. The expression vector containing each of these cDNAs and a second vector containing a neomycin or puromycin-resistance gene were introduced to HEK-293 or CHO cells by Lipofectin-Plus (Life Technology). Colonies were selected by growing transfected cells in the presence of neomycin or puromycin. Stably transfected cells were maintained in Dulbecco's modified Eagle's medium (DMEM) or F-12 medium with 10% fetal bovine serum, 100 µg/ml penicillin, 100 µg/ml streptomycin and appropriate concentrations of neomycin or puromycin. These stably transfected cells were referred to as HEK-"AdoR" or CHO-"AdoR" depending on the receptors that they express. The cell lines used routinely were CHO-$A_1$, HEK-$A_{2A}$, HEK-$A_{2B}$, and CHO-$A_3$ cells. In addition, hamster DDT1 MF-2 cells that express endogenous $A_1$ AdoRs were also used to determine the binding activities of compounds for $A_1$ AdoRs.

Membrane Preparation

Monolayers of transfected cells or DDT1 MF-2 were washed with phosphate buffered saline (PBS) and harvested in a buffer containing 10 mM HEPES (pH 7.4), 10 mM EDTA and protease inhibitors. The cells were homogenized in polytron for 1 minute at setting 4 and centrifuged at 29000 g for 15 minutes at 4° C. The cell pellets were washed with a buffer containing 10 mM HEPES (pH7.4), 1 mM EDTA and protease inhibitors, and were resuspended in the same buffer supplemented with 10% sucrose. Frozen aliquots were kept at −80° C.

Radioligand Binding

The affinities of compounds for $A_1$, $A_{2A}$, $A_{2B}$ or $A_3$ AdoRs were determined in competition studies using radioligands such as $^3$H—CPX ($A_1$ antagonist), or $^3$H—CCPA ($A_1$ agonist), $^3$H-ZM241385 ($A_{2A}$ antagonist) or $^3$H-CGS21680 ($A_{2A}$ agonist), $^3$H-ZM241385 ($A_{2B}$ antagonist) or $^{125}$I-AB-MECA ($A_3$ agonist) and membranes of corresponding cells. For example, to determine the affinity for $A_1$ AdoRs, the competition assays were started by mixing 0.5-1 nM $^3$H-CPX with various concentrations of test compounds and 25-100 µg membrane proteins of CHO-$A_1$ or DDT1 MF-2 in TE buffer (50 mM Tris and 1 mM EDTA) supplemented with 1 U/ml adenosine deaminase. The assays were incubated for 60-90 minutes, stopped by filtration onto GF/B filter plates using Packard Harvester and washed four times with ice-cold TM buffer (10 mM Tris, 1 mM MgCl2, pH 7.4). The amounts of radioligands that bound to the GF/B filter plates were determined by scintillation counting. Nonspecific binding were determined in the presence of 1-10 µM of cold ligands. $B_{max}$ and $K_D$ values were calculated using GraphPad software.

cAMP Measurements

Cells were harvested using 0.0025% trypsin and 2 mM EDTA in PBS, washed and resuspended in phenol-free DMEM to a concentration of $1 \times 10^6$ cells/ml, and then incubated with 1 U/ml of adenosine deaminase for 30 minutes at room temperature. Cells were then treated with various agonists, antagonists and/or forskolin in the presence or absence of 50 µM phosphodiesterase IV inhibitor, rolipram. After incubating for 5-30 minutes at 37° C., cells were lysed and cAMP concentrations were determined using cAMP-Screen Direct™ System (Applied Biosystem) according to the manufacturer's instructions.

The compounds of Formula I were shown to be $A_1$-adenosine receptor antagonists in this assay. The Ki (low) values for several of the compounds of the invention are presented in Table 1 below.

TABLE 1

| Corporate ID | Hamster-$A_1$[a] DDT1 MF-2 | Human-$A_1$[a] CHO-$A_1$ | Human-$A_{2A}$[b] HEK-$A_{2A}$ | Human-$A_{2B}$[c] HEK-$A_{2B}$ | Human-$A_3$[d] CHO-$A_3$ |
|---|---|---|---|---|---|
| cyclohexyl(9-ethyl-8-phenylpurin-6-yl)amine | 4 | 11 | >5000 | >6666 | 25.9 |
| [8-(3-chlorophenyl)-9-methylpurin-6-yl]cyclopentylamine | 3 | 5 | >5000 | >6666 | 42.30 |
| [8-(4-chlorophenyl)-9-methylpurin-6-yl]cyclopentylamine | 10 | 9 | >5000 | >6666 | 12.80 |
| 4-[6-(cyclopentylamino)-9-methylpurin-8-yl]phenol | 4 | 9 | >5000 | >6666 | 161.00 |
| cyclopentyl[8-(4-methoxyphenyl)-9-methylpurin-6-yl]amine | 22 | 32 | >5000 | >6666 | 47.30 |
| cyclopentyl[8-(4-fluorophenyl)-9-methylpurin-6-yl]amine | 1 | 5 | >5000 | >6666 | 175.00 |
| cyclopentyl[9-methyl-8-(3-methylphenyl)purin-6-yl]amine | 2 | 5 | >5000 | >6666 | 183.00 |
| cyclopentyl[9-methyl-8-(2-methylphenyl)purin-6-yl]amine | 20 | 42 | >5000 | >6666 | 11.40 |
| cyclopentyl[9-methyl-8-(4-methylphenyl)purin-6-yl]amine | 3 | 5 | >5000 | >6666 | 72.00 |
| cyclopentyl(9-methyl-8-(3-pyridyl)purin-6-yl)amine | 84 | 184 | >5000 | >6666 | 1040.00 |

TABLE 1-continued

| Corporate ID | Hamster-$A_1{}^a$ DDT1 MF-2 | Human-$A_1{}^a$ CHO-$A_1$ | Human-$A_{2A}{}^b$ HEK-$A_{2A}$ | Human-$A_{2B}{}^c$ HEK-$A_{2B}$ | Human-$A_3{}^d$ CHO-$A_3$ |
|---|---|---|---|---|---|
| cyclohexyl(8-phenyl-9-propylpurin-6-yl)amine | 11 | 25 | >5000 | >6666 | 122.00 |
| cyclohexyl(9-methyl-8-phenylpurin-6-yl)amine | 1 | 2 | >5000 | >6666 | 96.80 |

[a]Values determined using $^3$H-CPX radioligand
[b]Values determined using $^3$H-ZM241385 radioligand
[c]Values determined using $^3$H-CGS21680 radioligand
[d]Values determined using $^{125}$I-AB-MECA radioligand

What is claimed is:

1. A compound of the formula:

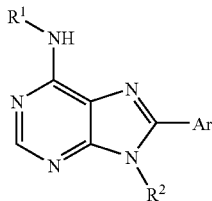

Formula I wherein:
R$^1$ is optionally substituted C$_3$-C$_8$ cycloalkyl; R$^2$ is hydrogen or C$_1$-C$_6$ alkyl; and Ar is optionally substituted aryl.

2. The compound of claim 1, wherein R$^1$ is optionally substituted C$_4$-C$_6$ cycloalkyl.

3. The compound of claim 2, wherein R$^2$ is C$_{1-4}$ alkyl.

4. The compound of claim 3, wherein Ar is optionally substituted monocyclic aryl.

5. The compound of claim 4, wherein R$^2$ is methyl, ethyl, or propyl.

6. The compound of claim 5, wherein R$^1$ is optionally substituted cyclopentyl, or optionally substituted cyclohexyl.

7. The compound of claim 6, wherein R$^2$ is methyl and Ar is phenyl.

8. The compound of claim 6, wherein R$^2$ is ethyl and Ar is phenyl.

9. The compound of claim 5, wherein R$^1$ is cyclobutyl, R$^2$ is methyl, and Ar is phenyl, namely, cyclobutyl(9-methyl-8-phenylpurin-6-yl)amine.

10. The compound of claim 5, wherein R$^1$ is cyclobutyl, R$^2$ is ethyl, and Ar is phenyl, namely, cyclobutyl(9-ethyl-8-phenylpurin-6-yl)amine.

11. The compound of claim 5, wherein R$^1$ is cyclobutyl, R$^2$ is propyl, and Ar is phenyl, namely, cyclobutyl(8-phenyl-9-propylpurin-6-yl)amine.

12. The compound of claim 6, wherein R$^1$ is cyclopentyl, R$^2$ is methyl, and Ar is phenyl, namely, cyclopentyl(9-methyl-8-phenylpurin-6-yl)amine.

13. The compound of claim 6, wherein R$^1$ is cyclopentyl, R$^2$ is ethyl, and Ar is phenyl, namely, cyclopentyl(9-ethyl-8-phenylpurin-6-yl)amine.

14. The compound of claim 6, wherein R$^1$ is cyclopentyl, R$^2$ is propyl, and Ar is phenyl, namely, cyclopentyl(8-phenyl-9-propylpurin-6-yl)amine.

15. The compound of claim 6, wherein R$^1$ is cyclohexyl, R$^2$ is methyl, and Ar is phenyl, namely, cyclohexyl(9-methyl-8-phenylpurin-6-yl)amine.

16. The compound of claim 6, wherein R$^1$ is cyclohexyl, R$^2$ is ethyl, and Ar is phenyl, namely, cyclohexyl(9-ethyl-8-phenylpurin-6-yl)amine.

17. The compound of claim 6, wherein R$^1$ is cyclohexyl, R$^2$ is propyl, and Ar is phenyl, namely, cyclohexyl(8-phenyl-9-propylpurin-6-yl)amine.

18. The compound of claim 6, wherein R$^1$ is cyclopentyl, R$^2$ is methyl, and Ar is 2-methylphenyl, namely, cyclopentyl [9-methyl-8-(2-methylphenyl) purin-6-yl]amine.

19. The compound of claim 6, wherein R$^1$ is cyclopentyl, R$^2$ is methyl, and Ar is 3-methylphenyl, namely, cyclopentyl [9-methyl-8-(3-methylphenyl) purin-6-yl]amine.

20. The compound of claim 6, wherein R$^1$ is cyclopentyl, R$^2$ is methyl, and Ar is 4-methylphenyl, namely, cyclopentyl [9-methyl-8-(4-methylphenyl) purin-6-yl]amine.

21. The compound of claim 6, wherein R$^1$ is cyclopentyl, R$^2$ is methyl, and Ar is 2-chlorophenyl, namely, [8-(2-chlorophenyl)-9-methylpurin-6-yl]cyclopentylamine.

22. The compound of claim 6, wherein R$^1$ is cyclopentyl, R$^2$ is methyl, and Ar is 3-chlorophenyl, namely, [8-(3-chlorophenyl)-9-methylpurin-6-yl]cyclopentylamine.

23. The compound of claim 6, wherein R$^1$ is cyclopentyl, R$^2$ is methyl, and Ar is 4-chlorophenyl, namely, [8-(4-chlorophenyl)-9-methylpurin-6-yl]cyclopentylamine.

24. The compound of claim 6, wherein R$^1$ is cyclopentyl, R$^2$ is methyl, and Ar is 4-fluorophenyl, namely, cyclopentyl [8-(4-fluorophenyl)-9-methylpurin-6-yl]amine.

25. The compound of claim 6, wherein R$^1$ is cyclopentyl, R$^2$ is methyl, and Ar is 4-methoxyphenyl, namely, cyclopentyl[8-(4-methoxyphenyl)-9-methylpurin-6-yl]amine.

26. The compound of claim 6, wherein R$^1$ is cyclopentyl, R$^2$ is methyl, and Ar is phenolyl, namely, 4-[6-(cyclopentylamino)-9-methylpurin-8-yl]phenol.

27. A pharmaceutical formulation, comprising a therapeutically effective amount of the compound of claim 1 and at least one pharmaceutically acceptable excipient.

28. A method of antagonizing A$_1$ adenosine receptors in a mammal, comprising administering to a mammal a therapeutically effective dose of the compound of claim 1.

29. The method of claim 28, wherein the A$_1$ adenosine receptor is antagonized in order to arrest the development of a clinical symptom of a condition and/or cause the regression of a clinical symptom of the condition, wherein the condition is selected from congestive heart failure, chronic renal disease that may be treated with a diuretic, cirrhosis, and any other disease that may be treated with a diuretic.

30. The compound 8-phenyl-9-propylpurine-6-ylamine.

* * * * *